US008742202B2

(12) United States Patent
Zhong

(10) Patent No.: US 8,742,202 B2
(45) Date of Patent: Jun. 3, 2014

(54) TRANSFORMATION OF SUGAR CANE

(75) Inventor: Heng Zhong, Chapel Hill, NC (US)

(73) Assignee: Syngenta Participations AG, Basel (CH)

( * ) Notice: Subject to any disclaimer, the term of this patent is extended or adjusted under 35 U.S.C. 154(b) by 227 days.

(21) Appl. No.: 13/139,515

(22) PCT Filed: Dec. 1, 2009

(86) PCT No.: PCT/US2009/066177

§ 371 (c)(1),
(2), (4) Date: Sep. 13, 2011

(87) PCT Pub. No.: WO2010/068521

PCT Pub. Date: Jun. 17, 2010

(65) Prior Publication Data

US 2011/0321199 A1 Dec. 29, 2011

(51) Int. Cl.
*C07K 14/415* (2006.01)
*A01H 1/04* (2006.01)
*C12N 15/87* (2006.01)

(52) U.S. Cl.
USPC ........... 800/278; 800/293; 800/294; 800/268; 800/320; 435/469; 435/459; 435/470; 435/430.1; 435/431

(58) Field of Classification Search
None
See application file for complete search history.

(56) References Cited

FOREIGN PATENT DOCUMENTS

WO 02/37951 5/2002

OTHER PUBLICATIONS

Snyman SJ et al., "Refining the application of direct embryogenesis in sugarcane: effect of the developmental phase of leaf disc explants and the timing of DNA transfer on transformation efficiency" Plant Cell Reports, Springer, Berlin, DE, vol. 25, No. 10 (Mar. 28, 2006) XP019423771.

Tiel et al. "Development of a system for rapid plant regeneartion fomr in vitro sugarcane(*Saccharum officinarum* L.) meristematic tissue", Biotecnologia Apliado (2006) 23:22-24 XP002563478.

Manickavasagam et al., "Agrobacterium-mediated genetic transformation and development of herbicide-resistant sugarcane (*Saccharum* species hybrids) using axiallary buds", Plant Cell (2004) 23:134-143 XP002344100.

Snyman, "Sugarcane Transformation" Transgenic Crops of the World—Essential Protocols, (2004) 103-114 XP8117538.

Snyman et al., "New Developments in the Production of Herbicide-Resistant Sugarcane", Proc. S. Afr Sug Technol Ass (2001) 75:112-114 XP002563482.

Snyman et al., "Direct Somatic Embryogenesis for Rapid, Cost Effective Production of Transgenic Sugarcane (*Saccharum* Spp. Hybrids)", Proc. S. Afr Sug Technol Ass (2001) 74: 186-187 XP002563483.

Gil et al., "Herbicide-resistant sugarcane (*Saccharum officinarum* L.) plants by Agrobacterium-mediatd transformation" Plants (1998) 206:20-27 XP002563432.

Arencibia et al., "An efficient protocol for sugarcane (*Saccharum* spp. L.) transformation mediated by *Agrobacterium tumefaciens*" Transgenic Research (1998) 7:213-222 XP008001638.

Latha et al., "Production of transgenic plants resistant to leaf blast disease in finger millet (*Eleusine coracana* (L>) (Gaertn.)" Plant Science (2005) 169:657-667 XP025296270.

Snyman et al., "Micropropagation of Sugarcane via Novacane Preliminary Steps in Commercial Application" Proc. S. Afr Sug Technol Ass (2008) 81:513-516 XP002563481.

Gill et al., "Direct plant regeneration from cultured young leaf segments of sugarcane", Plant Cell, Tissue and Organ Culture (2006) 84:227-231 XP002563480.

Lakshmanan et al., "Invited Review: Sugarcane's Biotechnology, the Challenges and Opportunities", Invitro Cell Dev. Biol.-Plant (2005) 41:345-363 XP009100033.

Snyman et al., "The Use of Sugarcane Leaf Roll Discs on Target Material and Regeneration of Transgenic Plants via Direct Embryogenesis: Problems and Potential", 10th IAPTC&B Congress Posters , p. 1460 XP008117246.

Lakshmanan et al., "Developmental and hormonal regulation of direct shoot organogenesis and somatic embryogenesis in sugarcane (*Saccharum* spp. interspecific hybrids) leaf culture", Plant Cell Rep (2006) 25:1007-1015 XP019423777.

*Primary Examiner* — David T Fox
*Assistant Examiner* — Jared Shapiro
(74) *Attorney, Agent, or Firm* — Yoshimi Barron

(57) ABSTRACT

Methods for the transformation of sugar cane are provided. The methods comprise utilizing sugar cane immature shoots as the source of plant material for transformation. Segments of the immature shoot are excised and transformed by any suitable transformation methodology. In some embodiments, the segments are cultured in embryogenic culture induction medium prior to transformation. Transformation can be performed via *Agrobacterium*-mediated gene delivery, biolistic transformation, and the like. Transgenic plants are regenerated from plantlets grown under conditions favoring growth of transformed cells while substantially inhibiting growth of non-transformed cells.

12 Claims, No Drawings

TRANSFORMATION OF SUGAR CANE

FIELD OF THE INVENTION

This invention relates to plant molecular biology, particularly to methods and compositions for the transformation of sugar cane.

BACKGROUND OF THE INVENTION

Sugar cane (*Saccharum* spp.) is a highly polyploid plant grown in different parts of the world from the tropics to the subtropics, and accounts for around 60% of the world's sugar. It is also one of the important cash crops in many developing/developed countries, with a high trade value. The importance of sugar cane has increased in recent years because cane is an important raw material for sugar industries and allied industries producing alcohol, acetic acid, butanol, paper, plywood, industrial enzymes and animal feed. Considering its importance in the agricultural industry, concerted efforts are being made for its improvement using biotechnological approaches.

The importance of sugar cane transformation is increasing as a means to introduce useful and improved traits into many cultivars of economical relevance for integrated crop management and biofuels applications. Some of the main traits to be improved by genetic engineering are: tolerances to viruses, insects, and fungus attacks, herbicide resistance, improvement of the fiber quality and the use of sugar cane plants as bioreactors.

The lack of a reproducible methodology for stable transformation of sugar cane has been an important obstacle to its genetic manipulation for many years. In 1992, Bower and Birch successfully recovered transgenic sugar cane plants from cell suspensions and embryogenic calli transformed by particle bombardment (Bower R and Birch R G The Plant J. 2(3):409-416 (1992)). Simultaneously, Arencibia et al Biotecnologia Aplicada 9, 156-65 (1992) developed a procedure for stable transformation of sugar cane by electroporation of meristematic tissue. Later, a method to produce transgenic sugar cane plants by intact cell electroporation was established by the same group (Arencibia et al. Plant Cell Reports 14, 305-9.1995). The development of herbicide-resistant plants containing the bar gene and derived from the commercial variety NCo 310 by biolistic transformation (Gallo-Meagher and Irvine Crop Sci 36:1367-1374 (1996) has been reported.

SUMMARY OF THE INVENTION

Methods for the transformation of sugar cane are provided. The methods comprise utilizing sugar cane immature shoots as the source of plant material for transformation. Segments of the immature shoots are excised and transformed by any suitable transformation methodology. In some embodiments, the segments are cultured in embryogenic culture induction medium prior to transformation. Transformation can be performed via *Agrobacterium*-mediated gene delivery, biolistic transformation, and the like. Transgenic plants are regenerated from plantlets grown under conditions favoring growth of transformed cells while substantially inhibiting growth of non-transformed cells.

The use of sugar cane immature shoots for transformation provides significant advantages over prior methodologies in that the plant can be induced into producing a large number immature shoots over a significant period of time, the immature shoots are an ideal source for transformation target material in the lab and transformation protocols do not require sacrifice of the plant nor substantial portion thereof in order to obtain the immature shoots for transformation. In addition, the immature shoots can be harvested from sugar cane plants that are very young in age.

BRIEF DESCRIPTION OF THE SEQUENCES IN THE SEQUENCE LISTING

Overview

Successful sugar cane regeneration and transformation has been reported using both particle- and *Agrobacterium*-mediated gene delivery methods. The explants used as targets for transformation are primarily embryogenic cultures derived from young leaf bases from the tops of 6-9 month old field or greenhouse grown plants or immature flowers of sugar cane plants. Auxiliary buds or shoot meristems from these tops are also used as targets for transformation. The transformation efficiency of sugar cane is reported as high as 35% using *Agrobacterium*-mediated transformation of embryogenic cultures (Manickavasagam, M et al. Plant Cell Rep. 23:134-143; 2004).

The present invention provides an alternative transformation target for recovery of transgenic sugar cane plants with a potential high transformation frequency in a very short time. The explants described herein are sugar cane immature shoots. For the purposes of the present invention, "sugar cane" will refer to any Saccharum plant or hybrid. Hybrid plants include those generated by the traditional *Saccharum spontaneum* by *Saccharum officianarum* hybrid material that makes up all current commercial sugar cane and energycane germplasm, and any other hybrids that are produced by crossing sugar cane with closely or distantly related species. Examples of other species that sugar cane can be crossed with to generate hybrid plants or new varieties of sugar cane include *Miscanthus* and *Sorghum*.

An "immature shoot" is any shoot less than about 6 months, less than about 5 months, less than about 4 months, less than about 3 months, less than about 2 months or less than about 1 month of age originating from the base or stool of the sugar cane plant close to the soil surface. An immature shoot may also be referred to as a primary, secondary, or side shoot. Sugar cane "setts" consist of stem pieces which contain one or several buds. Setts can be planted and will sprout a primary shoot in addition to secondary shoots or immature shoots.

Immature shoots grow up from the base of young or mature sugar cane plants and their production can be induced by cutting back the maturing canes near or to the ground, as well as removing larger immature shoots to promote growth of more immature shoots. A regular source of high quality immature shoots can be produced in large numbers in the greenhouse, making for a very consistent source of plant material for a transformation process. Use of immature shoots for transformation and regeneration of transgenic plants has a significantly reduced impact on the growth and development of the sugar cane plant. By continuously removing immature shoots before they reach maturity, the sugar cane plant is induced to continue to produce more immature shoots for a substantial length of time.

Immature shoots are collected from sugar cane plants that are less than about 24 months, less than about 23 months, less than about 22 months, less than about 21 months, less than about 20 months, less than about 19 months, less than about 18 months, less than about 17 months, less than about 16 months, less than about 15 months, less than about 14 months, less than about 13 months, less than about 12 months, less than about 13 months, less than about 10 months, less than about 9 months, less than about 8 months, less than about 7 months, less than about 6 months, less than about 5 months, less than about 4 months, less than about 3 months, less than about 2 months, or less than about 1 month of age. Alternatively, immature shoots are collected from sugar cane plants that are more than about 24 months, more than about 30 months, more than about 36 months or more than about 42 months of age. The sugar cane plants are greenhouse or field grown plants.

The article "a" and "an" are used herein to refer to one or more than one (i.e., to at least one) of the grammatical object of the article. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Explants

The methods of the present invention comprise transformation of sugar cane immature shoots with one or more nucleotide sequences of interest. Unless otherwise specified, immature shoots useful for the transformation methods disclosed herein are immature shoots at the development stage, i.e., where the lower internode is beginning to elongate. The age of the immature shoot at this stage is typically between about one week and six months old, including about one to about three months, about one to about four months, about one to about five months, about two to about three months, or about two to about four months old.

These immature shoots are excised from the plant and sterilized by standard methods as described herein and well known to those of ordinary skill in the art to establish sterile cultures in an artificial medium. For example, the immature shoots can be contacted with a 70% ethanol solution, or a 20% bleach solution. Following sterilization of the excised immature shoot, a segment, slice or section of plant tissue is obtained. The term "explant" refers to living tissue removed from an organism and placed in a medium for tissue culture. In some embodiments, the section may be about 0.1, about 0.2, about 0.3, about 0.4, about 0.5, about 0.6, about 0.7, about 0.8, about 0.9, about 1.0, about 1.5, about 2, about 3, about 4, about 5, or about 6 mm in thickness. The cut sections may be further cut horizontally.

This segment above the apical meristem that is excised from the immature shoot can be used as a target for transformation or cultured directly. Alternatively, the segment can be cut up in many different ways, such as cut longitudinally, cut horizontally, or cut into segments, to generate many explants as a target for transformation or source material for culture. The explant may be obtained from immature shoot tissues including leaf spindle or whorl, stems, leaf sheath, leaf roll (meristematic region), node, or internode segments. In some embodiments, the explant is leaf sheath or leaf roll sections. The segment may be cut from just above the apical meristem up to about 3 cm or up to about 6 cm above the apical meristem. In various embodiments, the explant is not a node segment or is not an internode segment. As used in the context of the invention, the term "node segment" includes any joint in a stem from where one or more leaves may grow and also includes any lateral (auxiliary) buds on the side of the stem, as in a leaf axil. The part of the stem between two nodes is termed the "internode." The outer one or two leaves may be removed from the immature shoot prior to segmenting.

Callus Induction

In some embodiments, the cut segments are cultured under conditions sufficient to induce embryogenic Culture response and produce embryogenic cultures or callus lines. The term "callus" refers to an undifferentiated proliferating mass of cells or tissue. In various embodiments, the media is suitable for embryogenic culture induction. The term "embryogenic culture" refers to tissue or cells that are undifferentiated and without significant structure but with the potential to form a more differentiated tissue (e.g., embryogenic tissue) that can produce somatic embryos or shoots and germinate into plants.

Culture conditions sufficient for embryogenic culture formation are known to those skilled in the art, and may vary according to sugar cane cultivar. Suitable media for establishment and maintenance of embryogenic cultures are described in, e.g. Wang ed. Methods in Molecular Biology Vol. 344, page 227-235; Published International Application No. WO 01/33943, U.S. Pat. No. 5,908,771, U.S. Pat. No. 6,242,257, Croy (Ed.) Plant Molecular Biology Labfax, Bios Scientific Publishers Ltd. (1993), Jones (Ed.) Plant Transfer and Expression Protocols, Humana Press (1995), and in the references cited therein. Each of these references is incorporated herein by reference in their entirety. Additional details relating to culturing plant cells, including pretreatment processes, are provided below in the examples.

The explant may be cultured from about 0 to about 90 days, inclusive, prior to transformation. In various embodiments, the explant is cultured for about 5 days, about 6 days, about 7 days, about 8, about 9, about 10, about 12, about 14, about 16, about 20, about 25, about 30 or up to 90 days prior to transformation. The culture medium may include Murashige & Skoog (MS) nutrient formulation (Murashige & Skoog, 1962, Physiologia Plantarum 473) or Gamborg's medium (Gamborg et al., 1968, Exp. Cell Res 50 15 1). Preferably, the medium comprises MS formulation. It will be appreciated that the above mentioned media are commercially available, as are other potentially useful media.

The medium may further comprise sucrose, and may additionally include agar. Thus, it will be appreciated that the explant may be cultured in solid or liquid medium.

Additional components of the medium may include phytohormones such as cytokinin and/or auxin. In various embodiments, the cytokinin is selected from the group consisting of kinetin, TDZ, and $N_6$-benzyladenine (BA). There are a variety of other cytokinins, or cytokinin-like, compounds which may be useful according to the present invention, for example zeatin, α-isopentyladenosine, and diphenylurea.

In various embodiments, the auxin is 1-napthaleneacetic acid (NAA) or 2,4 dichlorophenoxyacetic acid (2,4D). There are a variety of other auxins or auxin-like compounds which may be useful according to the present invention, for example dicamba, indole-3-butyric acid (IBA), p-chlorophenoxyacetic acid (CPA), indole-3-acetic acid (IAA), 2,4,5-trichlorophenoxyacetic acid, phenylacetic acid, picloram, β-napthoxyacetic acid, dicamba and trans-cinnamic acid.

It will be readily apparent to the skilled artisan that the most efficacious concentrations of auxin and/or cytokinin can be determined empirically by cross-testing various concentrations of auxin and cytokinin. The optimal concentration of either or both can be tailored according to the particular plant cultivar from which the cultured explant was taken.

Following initial embryogenic culture formation, high quality responses are optionally subcultured for about 1 to about 90 days, inclusive, to bulk up the callus for transformation. Embryogenic cultures are cultures composed of somatic embryos and/or cells that are differentiated to varying degrees. When induced to further differentiate and regenerate, shoots can arise from these cultures by either embryogenesis, organogenesis or some combination of these two processes.

In some embodiments of the invention, the embryogenic culture or callus is subsequently transformed with one or more nucleotide sequences of interest. The expression cassette described herein can be introduced into a cell of the embryogenic culture in a number of art-recognized ways. The term "introducing" in the context of a polynucleotide, for example, a nucleotide construct of interest, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

The variety of different explants that can be excised from the immature shoot can serve as either a target for immediate transformation or as a culture source to generate transformation target material. Explants can be immediately targeted for gene delivery by particle delivery, *Agrobacterium* or other methods of gene delivery. Alternatively, these explants can be placed into in vitro culture for some hours, days, weeks or months prior to targeting them for gene delivery. This culture period can produce an embryogenic culture line or/and callus that can also serve as a target for transformation.

Transformation

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant is intended the introduced polynucleotide is stably incorporated into the plant genome, and thus the plant is stably transformed with the polynucleotide.

"Stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the genes useful to this invention can be used in conjunction with any such vectors. Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells.

Many vectors are available for transformation using *Agrobacterium tumefaciens*. These typically carry at least one T-DNA border sequence and include vectors such as pBIN19 (Bevan, Nucl. Acids Res. (1984)). For the construction of vectors useful in *Agrobacterium* transformation, see, for example, US Patent Application Publication No. 2006/0260011, herein incorporated by reference.

Transformation techniques that do not rely on *Agrobacterium* include transformation via particle bombardment, protoplast uptake (e.g. PEG and electroporation) and microinjection.

In some embodiments, *Agrobacterium*-mediated transformation methods are employed. See, WO 94/00977 and U.S. Pat. No. 5,591,616, both of which are incorporated herein by reference. See also, Negrotto et al., Plant Cell Reports 19: 798-803 (2000), incorporated herein by reference. The term "*Agrobacterium*" refers to species, subspecies, or strains of the bacterium *Agrobacterium* that are able to mobilize and selectively transfer T-DNA into a plant cell. For example, the *Agrobacterium* is optionally *Agrobacterium rhizogenes*, but more typically is *Agrobacterium tumefaciens*. Suitable *Agrobacterium* strains include *Agrobacterium tumefaciens* and *Rhizobium rhizogenes* (*Agrobacterium rhizogenes*). While wild-type strains may be used, "disarmed" derivatives of both species, in which the tumor-inducing sequences of the Ti plasmid have been removed, are preferred. Suitable *Agrobacterium tumefaciens* strains include, e.g., EHA101, as described by Hood et al. ((1986) J. Bacteriol., 168: 1291-1301), LBA4404, as described by Hoekema et al. ((1983) Nature, 303: 179-80), and C58 (pMP90), as described by Koncz and Schell ((1986) Mol. Gen. Genet., 204: 383-96). Preferred *Agrobacterium rhizogenes* strain are 15834, as described by Birot et al. (Biochem, 25: 323-35) and R1000.

*Agrobacterium* transformation typically involves the transfer of the binary vector carrying the foreign DNA of interest to an appropriate *Agrobacterium* strain. Selection of the *Agrobacterium* strain may depend on the complement of vir genes carried by the host *Agrobacterium* strain either on a co-resident Ti plasmid or chromosomally (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid and which is able to mobilize the recombinant binary vector to the target *Agrobacterium* strain. Alternatively, the recombinant binary vector can be transferred to *Agrobacterium* by DNA transformation (Hofgen & Willmitzer, Nucl. Acids Res. 16: 9877 (1988)).

Transformation of the sugar cane immature shoot by recombinant *Agrobacterium* usually involves co-cultivation of the *Agrobacterium* with explants from the plant and follows protocols well known in the art. Transformed tissue is regenerated on selectable medium carrying the antibiotic or selectable marker present between the binary plasmid T-DNA borders.

Another approach useful for transformation involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

Other transformation techniques include direct gene transfer into protoplasts using PEG or electroporation techniques, and whiskers-mediated gene delivery into callus tissue. Transformations can be undertaken with a single DNA species or multiple DNA species (i.e. co-transformation) and both of these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093-1096 (1986)).

Another technique for transformation involves particle bombardment of excised explants directly or explants that have been cultured for some period of time or established embryogenic cultures. This includes either a high sucrose or a high maltose osmotic treatment step prior to gene delivery. Prior to bombardment, any number of targets are plated onto MS medium with sucrose (Murashiga & Skoog, Physiologia Plantarum 15: 473-497 (1962)) and phytohormone for induction of somatic embryos, which is allowed to proceed in the dark. On the chosen day of bombardment, targets are removed from the induction medium and placed onto the osmoticum. The addition of an osmoticum (i.e., a supplemental agent increasing osmolarity) to the culture/bombardment medium may dramatically increase the rate of transformation, although the optimum concentration for each cultivar may vary. Elevated osmoticum concentrations are thought to protect the cells from leakage or bursting and may also improve particle penetration. Suitable osmotica, such as mannitol, sorbitol and mixtures of these, are known by those skilled in the art. Osmoticum concentrations in MS medium of zero to 0.3M mannitol and zero to 0.3M sorbitol are suitable for culture/bombardment.

The targets are allowed to plasmolyze for 2-3 hours or more and are then bombarded. Twenty targets per target plate is typical, although not critical. An appropriate gene-carrying plasmid (such as pCIB3064 or pSOG35) is precipitated onto micrometer size gold particles using standard procedures. Each plate of targets is shot with, for example, the DuPont BIOLISTICS® helium device using a burst pressure of about 600 to about 1500 psi using a standard 80 mesh screen. After bombardment, the targets are placed back into the dark to recover for about 24 hours (still on osmoticum). After 24 hrs, the targets are removed from the osmoticum and placed back onto induction medium where they stay for about a month, with or without the addition of the appropriate selection agent, before regeneration. Approximately one month later the target explants with developing embryogenic culture are transferred to regeneration medium (MS+1 mg/liter NAA, 5 mg/liter GA), further containing the appropriate selection agent. After approximately one month, developed shoots are transferred to larger sterile containers known as "GA7s" which contain half-strength MS, 2% sucrose, and the same concentration of selection agent.

Selection

After transformation with the nucleotide sequence(s) of interest, the plant material is typically transferred to media that includes a selective agent that is capable of preventing the growth of cells that have not received a gene (e.g., a selectable marker) whose expression product is capable of preventing the action of the selective agent to thereby select for transformed plant cells. The term "selecting" refers to a process in which one or more plants or plant cells are identified as having one or more properties of interest, e.g., a selectable marker, enhanced insect resistance, increased or decreased carotenoid levels, altered coloration, etc. For example, a selection process can include placing organisms under conditions where the growth of those with a particular genotype will be favored.

The selection step comprises culturing the cells that were exposed to the nucleotide sequence of interest under selective conditions. The "selective conditions" include those that are sufficient for distinguishing a transformed cell from a non-transformed cell. Such conditions will vary with, for example, the type of selectable marker used, the cultivar, and the method of transformation, but will generally comprise conditions which favor the growth of transformed cells but inhibit the growth of non-transformed cells. In various embodiments, the selective conditions comprise those in which at least about 70%, at least about 80%, at least about 85%, at least about 90%, at least about 91%, at least about 92%, at least about 93%, about 94%, about 95%, about 96%, about 97%, about 98%, about 99% or greater of the cells growing under those conditions are transgenic.

In certain embodiments, for example, tissues are exposed to sublethal levels of selective agents for about 2-12 weeks, and then to lethal levels of selective agents for about 4-30 weeks in a step-wise selection process. A variety of selectable markers are known in the art and exemplary markers are described elsewhere herein. In certain embodiments, cells are transferred to a recovery medium that comprises counter-selective agents (e.g., antibiotics, etc.), e.g., to inhibit the growth of or kill *Agrobacterium* cells for a period of about 1-15 days, e.g., prior to or concurrently with being transferred to media comprising a selective agent. After a period of culture, plant cells that continue to grow normally are separated from cells whose growth has been slowed or terminated.

Regeneration

Plant tissue growing in the presence of selective agent may be further manipulated for plant regeneration. The term "regenerating" or "generating" refers to the formation of a plant that includes a rooted shoot. The regeneration of plants from various explants is well known in the art. See, e.g., Weissbach et al. (Eds.), Methods for Plant Molecular Biology, Academic Press, Inc. (1988). In certain embodiments of the invention, the regeneration and growth process includes the steps of selecting transformed cells and shoots, rooting the transformed shoots, and growing the plantlets in soil. For example, the regeneration of plants containing a gene introduced by *Agrobacterium* from leaf explants can be achieved as described by Horsch et al. (1985) Science, 227: 1229-1231. In this procedure, transformants are grown in the presence of a selection agent and in a medium that induces the regeneration of shoots in the plant species being transformed as described by Fraley et al. (1983) Proc. Natl. Acad. Sci. U.S.A., 80: 4803. This procedure typically produces shoots within two to four weeks and these transformed shoots are then transferred to an appropriate root-inducing medium containing the selective agent and an antibiotic to prevent bacterial growth. Typically, transformed shoots that rooted in the presence of the selective agent to form plantlets are then transplanted to soil or other media to allow the production of additional roots.

The transgenic plantlets are then propagated in soil or a soil substitute to promote growth into a mature transgenic plant. Propagation of transgenic plants from these plantlets is performed, for example, in Perlite, peatmoss and sand (1:1:1) under glasshouse conditions.

Detection of Transgene Expression

The above conditions lead to regeneration of green plantlets and plants with photosynthetic ability. As described above, a test used for confirmation that the gene is stably integrated into the genome of the host plant necessarily depends on the property to be conferred to the plant. For example, when the property is herbicide resistance, confirmation may be achieved by treatment of the growing plants by spraying or painting the leaves with the herbicide in a concentration that is lethal for control plants that have not been subjected to the transformation process.

In one embodiment, transgene expression is detected using an immunological method. Immunological methods which can be used include, but are not limited to, competitive and non-competitive assay systems using immune-based techniques such as Western blots, radioimmunoassays, ELISA (enzyme linked immunosorbent assay), multiplex ELISA, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. Such assays are routine and known in the art (see, e.g., Ausubel et al, eds, 1994, Current Protocols in Molecular Biology, Vol. I, John Wiley & Sons, Inc., New York, which is incorporated by reference herein in its entirety).

In addition to immunoassays, expression can be measured by evaluating patterns of expression of the transgene, or of reporter genes, or both. For example, expression patterns can be evaluated by Northern analysis, PCR, RT-PCR, Taq Man analysis, ribonuclease protection assays, FRET detection, monitoring one or more molecular beacons, hybridization to an oligonucleotide array, hybridization to a cDNA array, hybridization to a polynucleotide array, hybridization to a liquid microarray, hybridization to a microelectric array, cDNA sequencing, clone hybridization, cDNA fragment fingerprinting, and the like. The particular method elected will be dependent on such factors as quantity of RNA recovered, artisan preference, available reagents and equipment, detectors, and the like.

Plant Expression Cassettes

The methods of the invention comprise transformation of sugar cane with one or more nucleotide sequences of interest. In one embodiment, the nucleotide sequence encodes a polypeptide of interest. The nucleotide sequences may be present in DNA constructs or expression cassettes. "Expression cassette" as used herein means a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development.

The expression cassette may include in the 5'-3' direction of transcription, a transcriptional and translational initiation region (i.e., a promoter) and a polynucleotide of interest. The expression cassette may optionally comprise a transcriptional and translational termination region (i.e. termination region) functional in plants. In some embodiments, the expression cassette comprises a selectable marker gene to allow for selection for stable transformants. Expression constructs of the invention may also comprise a leader sequence and/or a sequence allowing for inducible expression of the polynucleotide of interest. See, Guo et al. (2003) Plant J. 34:383-92 and Chen et al. (2003) Plant J. 36:731-40 for examples of sequences allowing for inducible expression.

The regulatory sequences of the expression construct are operably linked to the polynucleotide of interest. By "operably linked" is intended a functional linkage between a promoter and a second sequence wherein the promoter sequence initiates and mediates transcription of the DNA sequence corresponding to the second sequence. Generally, operably linked means that the nucleotide sequences being linked are contiguous.

Any promoter capable of driving expression in the plant of interest may be used in the practice of the invention. The promoter may be native or analogous or foreign or heterologous to the plant host. The terms "heterologous" and "exogenous" when used herein to refer to a nucleic acid sequence (e.g. a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" nucleic acid (e.g. DNA) sequence is a nucleic acid (e.g. DNA or RNA) sequence naturally associated with a host cell into which it is introduced.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence.

Some suitable promoters initiate transcription only, or predominantly, in certain cell types. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et al., Plant Cell, 1:855-866 (1989); Bustos, et al., Plant Cell, 1:839-854 (1989); Green, et al., EMBO J. 7, 4035-4044 (1988); Meier, et al., Plant Cell, 3, 309-316 (1991); and Zhang, et al., Plant Physiology 110: 1069-1079 (1996).

Promoters active in photosynthetic tissue in order to drive transcription in green tissues such as leaves and stems are also contemplated for the present invention. Most suitable are promoters that drive expression only or predominantly in such tissues. The promoter may confer expression constitutively throughout the plant, or differentially with respect to the green tissues, or differentially with respect to the developmental stage of the green tissue in which expression occurs, or in response to external stimuli.

Examples of such promoters include the ribulose-1,5-bisphosphate carboxylase (RbcS) promoters such as the RbcS promoter from eastern larch (*Larix laricina*), the pine cab6 promoter (Yamamoto et al. (1994) Plant Cell Physiol. 35:773-778), the Cab-1 gene promoter from wheat (Fejes et al. (1990) Plant Mol. Biol. 15:921-932), the CAB-1 promoter from spinach (Lubberstedt et al. (1994) Plant Physiol. 104:997-1006), the cab 1 R promoter from rice (Loan et al. (1992) Plant Cell 4:971-981), the pyruvate orthophosphate dikinase (PPDK) promoter from corn (Matsuoka et al. (1993) Proc Natl Acad Sci USA 90:9586-9590), the tobacco Lhcb12 promoter (Cerdan et al. (1997) Plant Mol. Biol. 33:245-255), the *Arabidopsis thaliana* SUC2 sucrose-H+ symporter promoter (Truernit et al. (1995) Planta 196:564-570), and thylakoid membrane protein promoters from spinach (psaD, psaF, psaE, PC, FNR, atpC, atpD, cab, rbcS). Other promoters that drive transcription in stems, leafs and green tissue are described in U.S. Patent Publication No. 2007/0006346, herein incorporated by reference in its entirety.

A maize gene encoding phosphoenol carboxylase (PEPC) has been described by Hudspeth & Grula (Plant Molec Biol 12: 579-589 (1989)). Using standard molecular biological techniques the promoter for this gene can be used to drive the expression of any gene in a green tissue-specific manner in transgenic plants.

In some other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, chemicals such as ethanol or in response to light or drought.

A variety of transcriptional terminators are available for use in expression cassettes. These are responsible for the termination of transcription beyond the transgene and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. In addition, a gene's native transcription terminator may be used.

The expression cassette will comprise a selectable marker gene for the selection of transformed cells. The selectable marker gene may be on the same expression cassette as the nucleotide sequence of interest, or may be contransformed on a separate expression cassette. Selection markers used routinely in transformation include the nptll gene, which confers resistance to kanamycin and related antibiotics (Messing & Vierra. Gene 19: 259-268 (1982); Bevan et al., Nature 304: 184-187 (1983)), the bar gene, which confers resistance to the herbicide phosphinothricin (White et al., Nucl. Acids Res 18: 1062 (1990), Spencer et al. Theor. Appl. Genet. 79: 625-631 (1990)), the hph gene, which confers resistance to the antibiotic hygromycin (Blochinger & Diggelmann, Mol Cell Biol 4: 2929-2931), and the dhfr gene, which confers resistance to methatrexate (Bourouis et al., EMBO J. 2(7): 1099-1104 (1983)), the EPSPS gene, which confers resistance to glyphosate (U.S. Pat. Nos. 4,940,935 and 5,188,642), and the phosphomannose isomerase gene (PMI), which provides the ability to metabolize mannose (U.S. Pat. Nos. 5,767,378 and 5,994,629).

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. Intron 1 was found to be particularly effective and enhanced expression in fusion constructs with the chloramphenicol acetyltransferase gene (Callis et al., Genes Develop. 1: 1183-1200 (1987)). Intron sequences have been routinely incorporated into plant transformation vectors, typically within the non-translated leader.

A number of non-translated leader sequences derived from viruses are also known to enhance expression, and these are encompassed herein. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693-8711 (1987); Skuzeski et al. Plant Molec. Biol. 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus) (Allison et al., 1986); MDMV leader (Maize Dwarf Mosaic Virus); Virology 154:9-20); human immunoglobulin heavy-chain binding protein (BiP) leader, (Macejak, D. G., and Samow, P., Nature 353: 90-94 (1991); untranslated leader from the coat protein mRNA of alfalfa mosaic virus (AMV RNA 4), (Jobling, S. A., and Gehrke, L., Nature 325:622-625 (1987); tobacco mosaic virus leader (TMV), (Gallie, D. R. et al., Molecular Biology of RNA, pages 237-256 (1989); and Maize Chlorotic Mottle Virus leader (MCMV) (Lommel, S. A. et al., Virology 81:382-385 (1991). See also, Della-Cioppa et al., Plant Physiology 84:965-968 (1987).

Various mechanisms for targeting gene products are known to exist in plains and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104-15109 (1988)). These signal sequences can be fused to heterologous gene products to effect the import of heterologous products into the chloroplast (van den Broeck, et al. Nature 313: 358-363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

In order to ensure the localization in the plastids it is conceivable to use one of the following transit peptides: of the plastidic Ferredoxin: NADP+ oxidoreductase (FNR) of spinach which is enclosed in Jansen et al. (Current Genetics 13 (1988), 517-522). In particular, the sequence ranging from the nucleotides −171 to 165 of the cDNA sequence disclosed therein can be used, which comprises the 5' non-translated region as well as the sequence encoding the transit peptide. Another example is the transit peptide of the waxy protein of maize including the first 34 amino acid residues of the mature waxy protein (Klosgen et al., Mol. Gen. Genet. 217 (1989), 155-161). It is also possible to use this transit peptide without the first 34 amino acids of the mature protein. Furthermore, the signal peptides of the ribulose bisposphate carboxylase small subunit (Wolter et al., Proc. Natl. Acad. Sci. USA 85 (1988), 846-850; Nawrath et al., Proc. Natl. Acad. Sci. USA 91 (1994), 12760-12764), of the NADP malate dehydrogenase (Galiardo et al., Planta 197 (1995), 324-332), of the glutathione reductase (Creissen et al., Plant J. 8 (1995), 167-175) or of the R1 protein Lorberth et al. (Nature Biotechnology 16, (1998), 473-477) can be used.

Polypeptides of Interest

Polypeptides of interest that are suitable for expression in sugar cane include those resulting in agronomically-important traits such as herbicide resistance, virus resistance, bacterial pathogen resistance, insect resistance, nematode resistance, and fungal resistance. See, e.g., U.S. Pat. Nos. 5,569,823; 5,304,730; 5,495,071; 6,329,504; and 6,337,431. The polypeptide of interest may also be one that results in increases in plant vigor or yield (including polypeptides that allow a plant to grow at different temperatures, soil conditions and levels of sunlight and precipitation), or one that allows identification of a plant exhibiting a trait of interest (e.g., selectable marker gene, visual phenotypic variations, etc.).

In some embodiments, the transformed sugar cane exhibits resistance to an herbicide. A number of genes are available, both transgenic and non-transgenic, that confer herbicide resistance. Herbicide resistance is also sometimes referred to as herbicide tolerance. Genes conferring resistance to an herbicide that inhibits the growing point or meristem, such as an imidazalinone or a sulfonylurea can be suitable. Exemplary genes in this category code for mutant ALS and AHAS enzymes as described, for example, in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a gene encoding a mutant glutamine synthetase (GS) resistant to inhibition by herbicides that are known to inhibit GS, e.g. phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Genes for resistance to glyphosate are also suitable. See, for example, U.S. Pat. No. 4,940,835 and U.S. Pat. No. 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Genes for resistance to phosphono compounds such as glufosinate ammonium or phosphinothricin, and pyridinoxy or phenoxy propionic acids and cyclohexones are also suitable. See European application No. 0 242 246. See also, U.S. Pat. Nos. 5,879,903, 5,276,268 and 5,561,236.

Other suitable herbicides include those that inhibit photosynthesis, such as a triazine and a benzonitrile (nitrilase). See U.S. Pat. No. 4,810,648. Other suitable herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are genes that confer resistance to a protox enzyme, or provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Application No. 20010016956, and U.S. Pat. No. 6,084,155.

The insecticidal proteins useful for the invention may be expressed in an amount sufficient to control insect pests, i.e. insect controlling amounts. It is recognized that the amount of expression of insecticidal protein in a plant necessary to control insects may vary depending upon the sugar cane cultivar, type of insect, environmental factors and the like. Genes useful for insect or pest resistance include, for example, genes encoding toxins identified in *Bacillus* organisms. Genes encoding *Bacillus thuringiensis* (Bt) toxins from several subspecies have been cloned and recombinant clones have been found to be toxic to lepidopteran, dipteran and coleopteran insect larvae (for example, various delta-endotoxin genes such as Cry1Aa, Cry1Ab, Cry1Ac, Cry1B, Cry1C, Cry1D, Cry1Ea, Cry1Fa, Cry3A, Cry9A, Cry9C and Cry9B; as well as genes encoding vegetative insecticial proteins such as Vip1, Vip2 and Vip3). A full list of Bt toxins can be found on the worldwide web at .lifesci.sussex.ac.uk/home/Neil_Crickmore/Bt/.

The polypeptide of interest may also be useful for controlling a wide variety of pests including, but not limited to, *Ustilago scitaminea*, sugar cane mosaic virus, *Eldana saccharina, Diatraea saccharalis*, sorghum mosaic virus, etc.

Polypeptides of interest that are suitable for expression in sugar cane further include those that improve or otherwise facilitate the conversion of harvested cane into a commercially useful product, including, for example, increased or altered carbohydrate content and/or distribution, improved fermentation properties, increased oil content, increased protein content, improved digestability, and increased nutraceutical content, e.g., increased phytosterol content, increased tocopherol content, increased stanol content or increased vitamin content. Polypeptides of interest also include, for example, those resulting in or contributing to a reduced content of an unwanted component in a harvested crop, e.g., phytic acid, soybean trypsin inhibitor, or starch degrading enzymes, depending on the downstream use. By "resulting in" or "contributing to" is intended that the polypeptide of interest can directly or indirectly contribute to the existence of a trait of interest (e.g., increasing cellulose degradation by the heterologous expression of a starch degrading enzyme).

In one embodiment, the polypeptide of interest contributes to improved digestibility for food or feed. Xylanases are hemicellulolytic enzymes that improve the breakdown of plant cell walls which leads to better utilization of the plant nutrients by the animal. This leads to improved growth rate and feed conversion. Also, the viscosity of the feeds containing xylan can be reduced.

Numerous xylanases from fungal and bacterial microorganisms have been identified and characterized. (See, e.g., U.S. Pat. No. 5,437,992; Coughlin, M. P.; Biely, P. et al., Espoo 1993; P. Souminen and T. Reinikainen eds., Foundation for Biotechnical and Industrial Fermentation Research 8:125-135 (1993); U.S. Patent Application Publication No. 2005/0208178; and WO03/16654). In particular, three specific xylanases (XYL-I, XYL-II, and XYL-III) have been identified in *T. reesei* (Tenkanen, et al., Enzyme Microb. Technol. 14:566 (1992); Torronen, et al., Bio/Technology 10:1461 (1992); and Xu, et al., Appl. Microbiol. Biotechnol. 49:718 (1998)).

In another embodiment, the polypeptide of interest is a polysaccharide degrading enzyme. Such plants may be useful for generating, for example, femientation feedstocks for bioprocessing. In some embodiments, the enzymes useful for fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; and starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), β-glucosidase (EC 3.2.1.21); c) L-arabinases, such as endo-1,5-α-L-arabinase (EC 3.2.1.99), α-arabinosidases (EC 3.2.1.55) and the like; d) galactanases such as endo-1,4-β-D-galactanase (EC 3.2.1.89), endo-1,3-β-D-galactanase (EC 3.2.1.90), α-galactosidase (EC 3.2.1.22), β-galactosidase (EC 3.2.1.23) and the like; e) mannanases, such as endo-1,4-β-D-mannanase (EC 3.2.1.78), β-mannosidase (EC 3.2.1.25), α-mannosidase (EC 3.2.1.24) and the like; f) xylanases, such as endo-1,4-β-xylanase (EC 3.2.1.8), β-D-xylosidase (EC 3.2.1.37), 1,3-β-D-xylanase, and the like; g) other enzymes such as α-L-fucosidase (EC 3.2.1.51), α-L-rhamnosidase (EC 3.2.1.40), levanase (EC 3.2.1.65), inulanase (EC 3.2.1.7), and the like.

Another embodiment of the present invention encompasses the expression of heterologous starch degrading enzymes such as glucoamylase and amylase in the harvested plant material for downstream use in, for example, ethanol production. Glucoamylases (α-1,4-glucan glucohydrolases, E.C.3.2.1.3.) are starch hydrolyzing exo-acting carbohydrases. Glucoamylases catalyze the removal of successive glucose units from the non-reducing ends of starch or related oligo and polysaccharide molecules and can hydrolyze both linear and branched glucosidic linkages of starch (amylose and amylopectin). The term "alpha-amylase (e.g., E.C. class 3.2.1.1)" refers to enzymes that catalyze the hydrolysis of alpha-1,4-glucosidic linkages. These enzymes have also been described as those effecting the exo or endohydrolysis of 1,4-α-D-glucosidic linkages in polysaccharides containing 1,4-α-linked D-glucose units. Another term used to describe these enzymes is "glycogenase." Exemplary enzymes include alpha-1,4-glucan 4-glucanohydrase glucanohydrolase. Commercially, glucoamylases and amylases are very important enzymes that have been used in a wide variety of applications requiring the hydrolysis of starch.

Further additional enzymes which may be used include proteases, such as fungal and bacterial proteases. Fungal proteases include, for example, those obtained from *Aspergillus, Trichoderma, Mucor* and *Rhizopus*, such as *A. niger, A. awamori, A. oryzae* and *M. miehei*. Of particular interest in the present invention are cellobiohydrolase (CBH) enzymes (EC 3.2.1.91).

Other enzymes include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

It will also be recognized that the nucleotide sequence encoding the polypeptide of interest may be optimized for increased expression in the transformed host cell. That is, the nucleotide sequences can be synthesized using sugar cane-preferred codons for improved expression, or may be synthesized using codons at a sugar cane-preferred codon usage frequency. Generally, the GC content of the gene will be increased. See, for example, Campbell and Gowri (1990) Plant Physiol. 92:1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference.

EXPERIMENTAL

Example 1

Greenhouse Production of Sugar Cane Immature Shoots

Sugar cane immature shoots were readily produced in the greenhouse as a consistently high quality, readily available and relatively clean source material for cell cultures in the laboratory. Initially, sugar cane setts were planted in individual pots of appropriate soil mix in the greenhouse. These plants were grown for 12-18 months before soil was replaced. Plants were irrigated daily and liquid fertilizer was applied on a weekly basis to maintain ample supply of nutrients. Leaf tissue was trimmed back to one or two inches above the highest growth point on a biweekly basis. To induce immature shoot production, once the plant was well established from the sett, the primary shoot and any immature shoots that grew too large (larger than ¾ inch in diameter) were cut back to soil level to induce the plant to produce more immature shoots. The percentage of sand in the soil mixture was manipulated to encourage immature shoot production. Larger immature shoots were removed at soil level. Leaf rolls were excised from the immature shoots for use as target material or the initiation of embryogenic cultures for subsequent use as target material for transformation experiments. Cutting off the larger immature shoots also served to induce the production of additional immature shoots from the plants. High quality immature shoot production has continued for over one year and looks as if it can go on indefinitely, with proper care of the plants.

Example 2

Induction of Embryogenic Cultures

Sugar cane (Saccharum hybrid, cultivar will vary) stock plants were grown in the greenhouse. Immature shoots at the development stage where the lower internode is beginning to elongate were collected and sterilized by either spraying with 70% ethanol or immersing in 20% CLOROX® bleach (with 3 drops of Tween-20 per liter) for 20 minutes and rinsing 3 times with sterile tap water. Leaf rolls were then isolated from sterilized immature shoots by cutting 1-2 mm transverse sections from just above the apical meristem up to 2-3 cm above. The isolated leaf rolls were cultured on basal MS media plus 0.75-3 mg/L 2,4-D in the dark at 28° C. for 2-3 weeks. High quality embryogenic culture responses were then selectively subcultured to fresh media to serve as target material for transformation.

Example 3A

Microprojectile Bombardment-Mediated Transformation of Sugar Cane

Explant Pre-Treatment for Bombardment

Callus Pretreatment for Bombardment

For bombardment transformation, callus was selectively isolated from yellow and compact callus 3-6 weeks of age and 3-8 days after subculture and temporarily cultured on filter paper (Whatman #3 filter paper) in a plate with basal MS media contained 2 mg/L 2,4-D for over-night. The following morning, the high quality callus was selected and arranged in about 2-cm radii cenric ring on osmotic treatment media (Basal MS media with 2 mg/L 2,4-D+0.2 M sorbitol and 0.2 M mannitol or with 2 mg/L 2,4-D+0.25 M sorbitol) for 4 hours pre-treatment prior to bombardment.

Leaf Rolls Pretreatment for Bombardment

Leaf rolls pre-cultured on callus induction medium (basal MS media plus 2 mg/L 2,4-D) for 1, 3, 5, and up to 30 days were used for bombardment. Prior to bombardment, leaf rolls were arranged in about 2-cm radii centric ring on osmotic treatment media (Basal MS media with 2 mg/L 2,4-D+0.2 M sorbitol and 0.2 M mannitol) for 4 hours.

Particle Wash and DNA Coating

Particle Wash

Weighed 60 ing of 0.3-1.0 μm gold particles and suspended in 1 ml of 200 proof ethanol by sonication for 10 sec. and removed the supernatant carefully. The pellet was washed twice with 1 ml of sterile water, and resuspended in 1 ml of 50% sterile glycerol. Evenly aliquot 50 μl of gold-glycerol slurry into microfuge tubes and store the particles at −20° C.

DNA Coating

Add 1-5 μl of DNA (conc. 125-150 ng/per shot) to a tube of 50□l of gold particle-glycerol slurry. When vortexing, add 20 μl of glycerol, 50 ul of 2.5 M CaCl2.2$H_2O$, and 20 μl of 0.1-1 M of spermidine, sequentially. Keep vortexing for 3 min and spin down at high speed (13,000 rpm) for 10 sec. Remove the supernatant and wash with 250 μl of 200 proof ethanol by vortexing 2-3 sec. Spin down and remove supernatant, and finally suspended in 80 μl of 200 proof ethanol.

Bombardments

PDS-1000 Biolistc particle delivery system setting: sterilize the interior of the PDS Helium-1000 gene gun by spraying with 100% ethanol. Sterilize the macrocarrier holders and the red capplug with 100% ethanol and dry on the sterilized Petri dish. Sterilize the macrocarriers with 100% ethanol in Petri dish, dry and mount them to the macrocarrier holders using the red capplug. Sterilize 200×200 stopping screen with 100% ethanol in Petri dish and dry. Sterilize the rupture discs with 100% ethanol in Petri dish and dry. The setting of the Biolistic device are as follows: secure the rupture disc holder containing a 1100-1350 psi, preferable 1100 psi, rupture disc at the end of the gas acceleration tube. Set the distance between the rupture disc and macrocarrier at 8 mm, macrocarrier and stopping screen at 10 mm, and the distance between stopping screen and target at 7 cm. Set the pressure of the helium tank at least 100 psi more than the rupture disc.

For bombardment, 100 ng-1 μg of whole plasmid DNA (digested or un-digested) were loaded to each particle tube (3 mg gold). Each tube was aliquot out to 6 shots.

Two shots were used for each plate of treated callus. The bombarded callus was kept at the osmotic media for one hour and then transferred to callus recovery media or remain on the osmotic media for overnight then transferred to recovery media (MS basal media with 2 mg/L 2,4-D).

Recovery and Selection Culture

The bombarded callus was placed on recovery media for 5-7 days and then transferred to PMI selection media with 20, 15, 10, and 5 g/L sucrose and 3 g/L, 4 g/L, 5 g/L, 6 g/L and 7 g/L mannose, respectively. The callus tissues were sub-cultured for 2-3 weeks at the same selection level (PMI). All cultures were kept in the dark at 28° C.

Plant Regeneration from Putative Transgenic Events

Based on plant regeneration experiments from sugar cane, the PMI resistant events were carefully isolated from these cultures on PMI selection media and transferred to plant regeneration media (basal MS salts and B5 vitamins supplemented with 2 mg/L BAP) and maintained in dark for two more weeks, then moved to light culture room (16/8 light-dark period) at 28° C. After 2-4 weeks in regeneration media, putative transgenic plants were regenerated from these stable callus events.

Example 3B

Results and Summary of Microprojectile Experiments to Date

A total of 21 bombardment experiments (3 constructs and 6 genotypes) have been carried out. The results are given in the following tables.

Different Gold Particle Sizes

Three gold particle sizes (See table 1) were used in sugar cane biolistics transformation. Three to five experiments were carried out with each particle size. After 2-3 months, stable callus events with CFP fluorescence under an UV microscope were counted. Over 50 plants were analyzed by ELISA and TaqMan. Total of 40 transgenic plants (frequency of transgenic plants in total plants analyzed was 80%) were sent to greenhouse. The average results were given in the Table 1.

TABLE 1

Effect of different gold particle size on stable callus events (Construct: p12672)

| Genotype | Particle size | No. of callus per exp†. | Stable callus events after 3 months from each experiment | Plants analyzed by ELISA or TaqMan | Transgenic plants in Greenhouse |
|---|---|---|---|---|---|
| L97-128 | 1.0 μm | 120-140 | 25-40 | 27 | 20 |
| L97-128 | 0.6 μm | 120-140 | 25-45 | 25 | 19 |
| L97-128 | 0.3 μm | 120-140 | 30-60 | ND‡ | |

†No. of callus was estimated in each transformation by a target plate × transferred plates after bombardment × callus numbers per plate. The callus of each target was transferred to 3-4 plates depending on callus size. Each plate contains 16 calli ‡ND not determined 2. Different Genotypes Six different genotypes (see Table 2) of sugar cane were tested in biolistics transformation. One to two transformation experiments were carried out for each genotype of sugar cane. The average results are given in the Table 2.

TABLE 2

Transgenic plants recovered from various sugar cane genotypes (Construct: p12672).

| Genotype | Particle size | No. of exp. | No. of callus per exp.* | Stable callus events after 3 months from each experiment | Plants analyzed by ELISA or Taqman | Transgenic plants sent to Green-house |
|---|---|---|---|---|---|---|
| L97-128 | 0.6 μm | 2 | 120-140 | 35 ± 8 | 25 | 21 |
| L99-226 | 0.6 μm | 2 | 120-140 | 30 ± 9 | 1 | 1 |
| L99-233 | 0.6 μm | 2 | 120-140 | 30 ± 11 | 4 | 2 |
| SP70-1143 | 0.6 μm | 2 | 120-140 | 25 ± 9 | 5 by CFP fluorescence | |
| CP84-1198 | 0.6 μm | 1 | 120-140 | 38 | 7 by fluorescence | |
| TCP72-1210 | 0.6 μm | 1 | 120-140 | 35 | 2 by fluorescence | |

*No. of callus was estimated in each transformation by a target plate × transferred plates after bombardment × callus numbers per plate. The callus of each target was transferred to 3-4 plates depending on callus size. Each plate contains 16 calli.

Example 4

*Agrobacterium*-Mediated Transformation in Sugar Cane

1. Transformation vector and *Agrobacterium* strains: Binary vectors in *Agrobacterium tumefaciens* strain such as LB4404 or EHA101 were used for transformation. A small amount of the Agro from the vial stored in −80° C. was taken with a sterile disposable plastic inoculating loop and placed on a plate. Agro was spread with the loop or cell spreader, to create a thin layer of cells over the surface of the growth media. Plates were placed in the 28° C. incubator for ~2 days prior to use. *Agrobacterium* cells were collected from the plate using a disposable plastic inoculation loop and suspended in liquid infection medium, for example SCInoc, in a sterile disposable plastic tube. The tube was vortexted until *Agrobacterium* cells were uniformly dispersed in the suspension. Light absorption of the bacterial suspension was measured in a spectrophotometer and diluted to A660 of 0.1-0.85. Acetosyringone was added to a final concentration of 40-80 mg/L (200-400 uM) to induce virulence gene expression.
2. Preparation of embryogenic culture transformation targets: embryogenic cultures were induced as described in example 2. The best quality target pieces were visually selected from the embryogenic culture lines for use in transformation.
3. Infection and co-cultivation: The prepared explants were immediately infected with *Agrobacterium* by mixing the isolated embryogenic culture explants with bacterial suspension. Various pretreatment may be applied to the target tissue in order to make the plant cells more amenable to gene delivery such as heat shock etc. The mixture was incubated for at least 1 minute or up to overnight at room temperature. Various treatments may be applied during inoculation to improve contact between bacteria and plant cells, such as sonication, vacuum infiltration etc. Following infection, the explants were removed from the *Agrobacterium* suspension and placed on a co-cultivation medium such as SCCoCult with or without a paper filter. The co-cultivation plates were incubated for 3 to 5 days at 20-28° C. in the dark.
4. Regeneration and Selection of Transgenic Plants: After co-cultivation, embryogenic target pieces were transferred to recovery medium without selection agent such as SCRecov with appropriate antibiotics to inhibit *Agrobacterium* growth. The recovery plates with the explants were incubated for 2-10 days at 28° C. in the dark. After the recovery period, the explants were transferred to pre-regeneration selection media such as SCM (with appropriate antibiotics) and were cultured at 28° C. in the dark for 3 weeks. After 3-5 weeks in pre-regeneration/selection media any proliferating sectors were selectively subcultured to regeneration/selection media SCManRegen (with appropriate antibiotics) for regeneration induction. These were cultured at 28° C. in the dark for 1 week. Regeneration induction plates were then moved to be cultured in the light at 28° C. with 16 hr/day light. After 2 weeks, developing shoots were transferred to Plant containers with SCR media for shoot elongation and rooting.
5. Transformation results Transgenic sugar cane shoots were obtained using embryogenic culture as explants. In one experiment where sugar cane embryogenic culture was transformed with *Agrobacterium tumefaciens* containing the CFP gene, 10 out of 250 pieces of callus produced CFP positive stable callus. Shoots were regenerated from the stable events.

Media Formulations:

| Name of Chemical | Amount | Units |
|---|---|---|
| Recipe Name SC2D<br>Final pH 5.8<br>Recipe for 1 L | | |
| MS Basal Salt Mixture | 4.3 | g |
| B5 Vitamins 200X | 5 | ml |
| Sucrose | 30 | g |
| 2,4-D 1 mg/ml | 2 | ml |
| Phytablend | 7 | g |
| Recipe Name SCInoc<br>Final pH 5.3<br>Recipe for 1 L | | |
| MS Basal Salt Mixture | 4.3 | g |
| B5 Vitamins 200X | 5 | ml |
| Sucrose | 88.5 | g |
| Glutamine 50 mg/ml | 17.5 | ml |
| Glucose | 36 | g |
| 2,4-D 1 mg/ml | 1 | ml |

-continued

| Name of Chemical | Amount | Units |
|---|---|---|
| Arginine | 174 | mg |
| Glycine 1 mg/ml | 7.5 | ml |
| Aspartic Acid | 266 | mg |
| Casein Hydrolysate Enzymatic | 500 | mg |
| Acetosyringone 40 mg/ml | 1 | ml |
| Recipe Name SCCoCult<br>Final pH 5.3<br>Recipe for 1 L | | |
| MS Basal Salt Mixture | 4.3 | g |
| B5 Vitamins 200X | 5 | ml |
| Sucrose | 30 | g |
| Glutamine 50 mg/ml | 17.5 | ml |
| Glucose | 30 | g |
| 2,4-D 1 mg/ml | 1 | ml |
| Arginine | 174 | mg |
| Glycine 1 mg/ml | 7.5 | ml |
| Phytagel | 3 | g |
| Aspartic Acid | 266 | mg |
| Casein Hydrolysate Enzymatic | 500 | mg |
| Recipe Name SCRecov<br>Final pH 5.8<br>Recipe for 1 L | | |
| MS Basal Salt Mixture | 4.3 | g |
| B5 Vitamins 200X | 5 | ml |
| Sucrose | 30 | g |
| 2,4-D 1 mg/ml | 2 | ml |
| Phytablend | 7 | g |
| Ticarcillin potassium clavulanate 15:1 100 mg/ml | 2.5 | ml |
| Recipe Name SCMan<br>Final pH 5.8<br>Recipe for 1 L | | |
| MS Basal Salt Mixture | 4.3 | g |
| B5 Vitamins 200X | 5 | ml |
| Sucrose | 20 | g |
| 2,4-D 1 mg/ml | 2 | ml |
| Phytablend | 7 | g |
| Mannose 1 g/ml | 3 | ml |
| Ticarcillin potassium clavulanate 15:1 100 mg/ml | 2.5 | ml |
| Recipe Name SCManRege<br>Final pH 5.8<br>Recipe for 1 L | | |
| MS Basal Salt Mixture | 4.3 | g |
| B5 Vitamins 200X | 5 | ml |
| Sucrose | 24 | g |
| BA 1 mg/ml | 2 | ml |
| Phytablend | 7 | g |
| Mannose 1 g/ml | 3 | ml |
| Recipe Name SCR<br>Final pH 5.8<br>Recipe for 1 L | | |
| MS Basal Salt Mixture | 4.3 | g |
| B5 Vitamins 200X | 5 | ml |
| Sucrose | 20 | g |
| Phytablend | 7.0 | g |
| NAA 1 mg/ml | 0.5 | ml |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

1. A method of producing transformed sugar cane plant cells comprising introducing a nucleotide sequence of interest into at least one cell obtained from a sugar cane immature shoot.

2. The method of claim 1, wherein the nucleotide sequence of interest is introduced via particle bombardment.

3. The method of claim 1, wherein the nucleotide sequence of interest is introduced via *Agrobacterium*-mediated gene delivery.

4. The method of claim 1, wherein the cell obtained from a sugar cane immature shoot is obtained from a leaf roll segment excised from said immature shoot.

5. The method of claim 1, wherein the cell obtained from the sugar cane immature shoot is obtained from a leaf sheath segment excised from said immature shoot.

6. The method of claim 4 or 5, wherein said segment is from about 0.1 to about 3.0 cm in thickness.

7. The method of claim 6, wherein said section is from about 0.5 mm to about 3 cm in thickness.

8. The method of claim 1, wherein the cell obtained from the sugar cane immature shoot is obtained by culturing a segment of said sugar cane immature shoot for a period of time prior to or after transformation.

9. The method of claim 8, wherein said period of time is from about 0 to about 90 days.

10. The method of claim 9, wherein said period of time is from about 5 to about 21 days.

11. The method of claim 8, wherein said cell is cultured in a medium comprising a cytokinin.

12. The method of claim 11, wherein said cytokinin is kinetin, TDZ, zeatin, or N6-benzyladenine (BA).

13. The method of claim 8, wherein said cell is cultured in a medium comprising an auxin.

14. The method of claim 13, wherein said auxin is 1-napthaleneacetic acid (NAA), Dicamba, indole-3-Acetic Acid (IAA), indole-3-Butyric Acid (IBA) or 2,4-dichlorophenoxyacetic acid (2,4-D).

15. The method of claim 1, wherein said nucleotide sequence of interest is contained within an expression cassette.

16. The method of claim 15, wherein said expression cassette further comprises a selectable marker gene.

17. The method of claim 16, wherein said selectable marker gene is phosphomannose isomerase (PMI).

18. The method of claim 1, wherein said immature shoot is between one week and six months of age.

19. The method of claim 8, wherein said culturing produces an embryogenic culture, and said cell is obtained from said callus.

20: A method of producing transformed sugar cane plant cells comprising:

a) obtaining a segment of plant tissue from a sugar cane immature shoot;

b) culturing said segment under conditions sufficient for embryogenic culture formation;

c) introducing into said embryogenic culture an expression cassette comprising a nucleotide sequence of interest;

d) culturing the embryogenic culture of (c) under selective conditions, wherein said conditions are sufficient for distinguishing a transformed cell from a non-transformed cell; and, e) regenerating a transformed plant 21. The method of claim 20, wherein the nucleotide sequence of interest is introduced via particle bombardment.

22. The method of claim 20, wherein the nucleotide sequence of interest is introduced via *Agrobacterium*-mediated gene delivery.

23. The method of claim 20, wherein the cell obtained from a sugar cane immature shoot is obtained from a leaf roll segment excised from said immature shoot.

24. The method of claim 20, wherein the cell obtained from the sugar cane immature shoot is obtained from a leaf sheath segment excised from said immature shoot.

25. The method of claim 23 or 24, wherein said segment is from about 0.1 to about 1.0 mm in thickness.

26. The method of claim 25, wherein said section is from about 0.5 to about 1 mm in thickness.

27. The method of claim 20, wherein the culturing in step (b) is from about 1 to about 30 days.

28. The method of claim 27, wherein the culturing in step (b) is from about 14 to about 21 days.

29. The method of claim 20, wherein the culturing in step (b) is performed in a medium comprising a cytokinin.

30. The method of claim 29, wherein said cytokinin is kinetin, TDZ, zeatin or N6-benzyladenine (BA).

31. The method of claim 29 or 30, wherein said medium further comprises an auxin.

32. The method of claim 31, wherein said auxin is 1-napthaleneacetic acid (NAA), Dicamba, indole-3-Acetic Acid (IAA), indole-3-Butyric Acid (IBA) or 2,4-dichlorophenoxyacetic acid (2,4-D).

33. The method of claim 20, wherein said expression cassette further comprises a selectable marker gene.

34. The method of claim 33, wherein said selectable marker gene is phosphomannose isomerase (PMI).

35. The method of claim 34, wherein said immature shoot is between one week and six months of age.

What is claimed is:

1. A method of producing transformed sugar cane plant cells comprising:

a) obtaining a segment of plant tissue from a sugar cane immature shoot, wherein said segment is obtained by excising a leaf sheath segment or a leaf roll segment from said immature shoot;

b) culturing said segment under conditions sufficient for embryogenic culture formation, wherein said culturing is performed in a medium comprising an auxin and culturing is for a period of 14 to 30 days;

c) introducing into said embryogenic culture an expression cassette comprising a nucleotide sequence of interest;

d) culturing the embryogenic culture of (c) under selective conditions, wherein said conditions are sufficient for distinguishing a transformed cell from a non-transformed cell; and, e) regenerating a transformed plant.

2. The method of claim 1, wherein the nucleotide sequence of interest is introduced via particle bombardment.

3. The method of claim 1, wherein the nucleotide sequence of interest is introduced via *Agrobacterium*-mediated gene delivery.

4. The method of claim 1, wherein said segment is from 0.1 to 1.0 mm in thickness.

5. The method of claim 4, wherein said segment is from 0.5 to 1 mm in thickness.

6. The method of claim 1, wherein the culturing in step (b) is performed in a medium further comprising a cytokinin.

7. The method of claim 6, wherein said cytokinin is kinetin, TDZ, zeatin or $N_6$-benzyladenine (BA).

8. The method of claim 1, wherein said auxin of step (b) is 1-napthaleneacetic acid (NAA), Dicamba, indole-3-Acetic Acid (IAA), indole-3-Butyric Acid (IBA) or 2,4-dichlorophenoxyacetic acid (2,4-D).

9. The method of claim 1, wherein said expression cassette further comprises a selectable marker gene.

10. The method of claim 9, wherein said selectable marker gene is phosphomannose isomerase (PMI).

11. The method of claim 10, wherein said immature shoot is between one week and six months of age.

12. The method of claim 1, wherein said nucleotide sequence of interest is contained within an expression cassette.

* * * * *